United States Patent [19]

Henderson

[11] Patent Number: 4,661,407
[45] Date of Patent: Apr. 28, 1987

[54] GLASS-SURFACE MICROCARRIER FOR ANCHORAGE-DEPENDENT CELL CULTIVATION

[75] Inventor: Timothy M. Henderson, Ann Arbor, Mich.

[73] Assignee: KMS Fusion, Inc., Ann Arbor, Mich.

[21] Appl. No.: 790,952

[22] Filed: Oct. 24, 1985

Related U.S. Application Data

[62] Division of Ser. No. 689,488, Jan. 7, 1985, Pat. No. 4,564,532.

[51] Int. Cl.$^4$ .......................... B32B 5/16; C12N 5/00; C12N 5/02; C12N 11/14
[52] U.S. Cl. ........................................ 428/403; 427/2; 428/406; 428/407; 435/176; 435/241
[58] Field of Search .................... 427/2; 435/176, 240, 435/241; 428/403, 406, 407

[56] References Cited

U.S. PATENT DOCUMENTS

| | | | |
|---|---|---|---|
| 4,448,884 | 5/1984 | Henderson | 435/241 |
| 4,540,629 | 9/1985 | Sands et al. | 428/406 X |
| 4,549,892 | 10/1985 | Baker et al. | 428/406 X |

Primary Examiner—Michael R. Lusignan
Attorney, Agent, or Firm—Barnes, Kisselle, Raisch, Choate, Whittemore & Hulbert

[57] ABSTRACT

A chemical vapor deposition process for making glass-surfaced microcarriers, and the resulting product, in which hollow spherical micro-sized shells of glass or ceramic composition replaced within a fluidized bed coater, and separate preheated reaction gasses are directed into the coater bed. The shell precursors have a preferred starting density of not more than the predetermined desired final density in the range of 1.01 to 1.2 g/cc, and have a diameter in the range of 5 to 500 μm, preferably 105 to 150 μm. The thickness of the silicate glass coating is preferably in the range of 11 to 16 μm. An alternative embodiment employs solid precursor beads of polyphenylene oxide.

5 Claims, 1 Drawing Figure

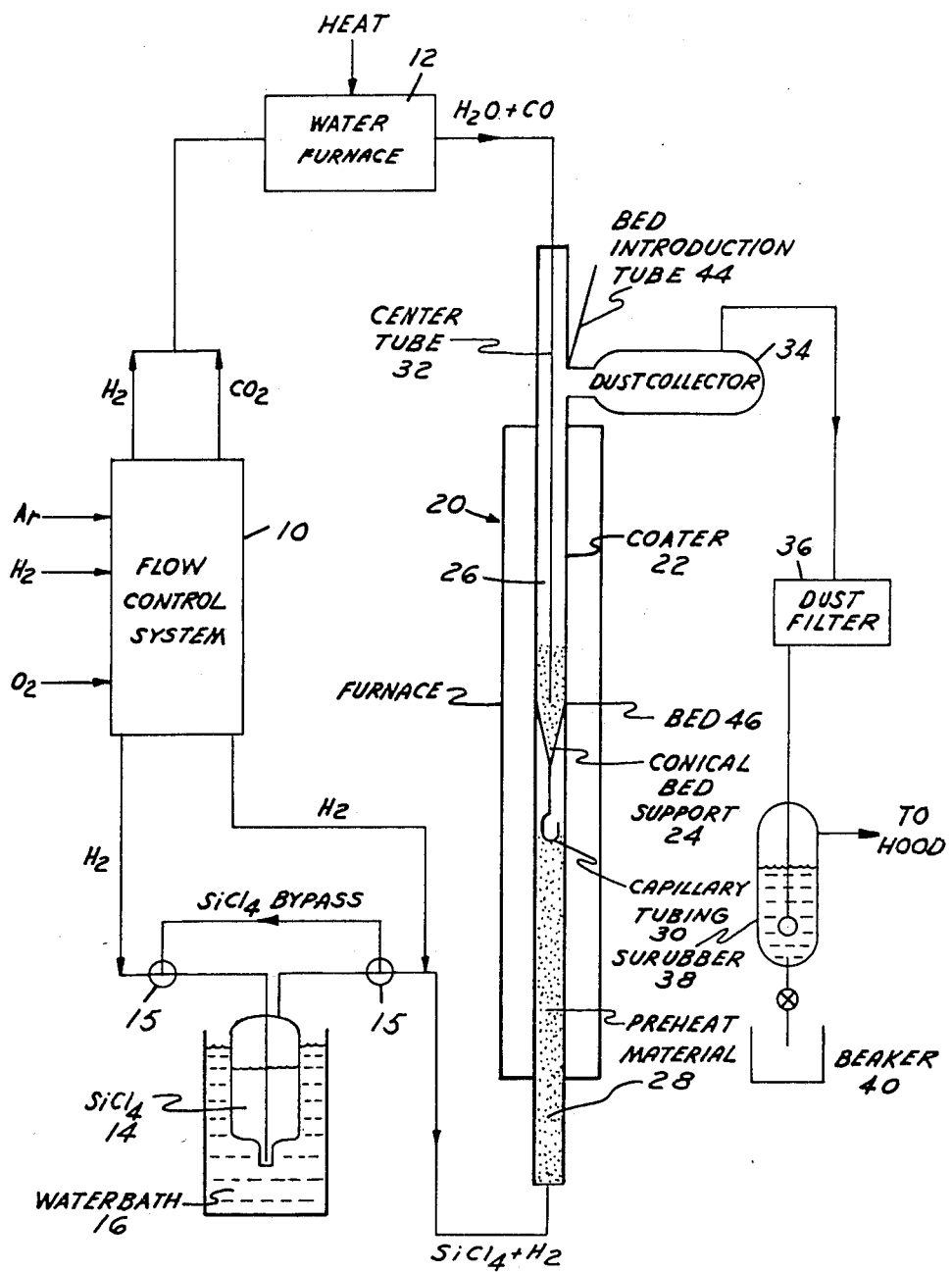

GLASS-SURFACE MICROCARRIER FOR ANCHORAGE-DEPENDENT CELL CULTIVATION

This application is a division of my copending application, Ser. No. 689,488, filed Jan. 7, 1985, now U.S. Pat. No. 4,564,532, patented Jan. 14, 1986.

The present invention relates to microcarriers for growth of anchorage-dependent cell cultures. More particularly, the invention relates to glass-surface microspheres specifically adapted for use as microcarriers, and to methods for manufacture of such microspheres.

BACKGROUND OF THE INVENTION

Anchorage-dependent cell cultivation requires provision of an attachment surface onto which the cultivated cells may anchor and grow. Cell production depends, among other factors, upon the amount of surface area available for cell attachment. It has heretofore been proposed to increase available surface area by replacing standard roller bottle and petrie dish glass attachment surfaces with a stationary bed of solid glass beads (density $\simeq 2.3$ g/cc) around and through which the nutrient medium is continuously circulated. It has also been proposed to increase attachment surface-to-volume ratio, and thus increase production efficiency, by employing so-called microcarriers which remain in suspension under continuous agitation in the culture medium.

Most typically, the proposed microcarriers are in the form of porous plastic (dextran) beads. Plastic microcarriers of this type require alteration of electrically charged surface moieties to promote cell attachment, which alteration is difficult to control quantitatively in production, and is toxic to some fastidious types of cell cultures if not properly controlled. The porous plastic beads absorb cell nutrients and metabolic wastes. Moreover, cell pseudopods attach and cling to pores and suface irregularities, making harvesting of the cells and cleansing and reuse of the plastic microcarriers most difficult. The art relative to provision of attachment surfaces for anchorage-dependent cell cultivation is surveyed in Levine et al, "Optimizing Parameters for Growth of Anchorage-Dependent Mammalian Cells in Microcarrier Cultures", *Cell Culture and Its Application,* Action Ed., Academic Press (1977), pp. 191–216, and in 3rd General Meeting of ESACT, Oxford 1979, *Develop. Biol. Standard,* 46, pp. 109–294 (S. Karger, Basel 1980).

In the copending U.S. application of Downs et al, Ser. No. 332,377 filed Dec. 21, 1981, now abandoned, and assigned to the assignee hereof, the foregoing and other difficulties in the microcarrier arts are addressed by forming hollow precursor microspheres of silicate glass composition, and then tailoring the density of such precursor microspheres in a post-forming etching operation to match closely the density of the desired aqueous growth medium, usually in the range of 1.01 to 1.09 g/cc. Microcarriers so formed have proven successful in overcoming the surface-charge, buoyancy, harvesting and reuse problems of the earlier art. However, the number of separate manufacturing operations involved has made cost reduction desirable.

U.S. Pat. No. 4,448,884 to the inventor herein and assigned to the assignee hereof discloses a further step forward in the art wherein microcarriers for anchorage-dependent cell cultivation are prepared to contain a spherical substrate of polymeric material having a bulk density of about 1 g/cc so as to be substantially buoyant in an aqueous culture medium, and a thin (less than 1 $\mu$m) coating layer of silicate glass. The silicate glass coating layer is preferably applied to a spherical precursor of polymeric material in an rf sputtering operation. An intermediate coating layer of magnetic material may be deposited prior to the silicate glass layer, so that the microcarriers may be readily removed from culture media by suitable subjection to a magnetic field.

OBJECTS AND SUMMARY OF THE INVENTION

A general object of the present invention, therefore, is to provide a microcarrier having a density which closely matches that of typical cell culture media, which embodies the desirable surface characteristics of silicate glass, but which is less expensive to manufacture than are microcarriers previously proposed which embody similar benefits.

Another object of the invention is to provide a method of manufacturing such microcarriers, and particularly a method in which density of the resulting microcarrier may be closely controlled within the range of about 1.01 to 1.2 g/cc.

Briefly stated, glass-surface microcarriers for anchorage-dependent cell cultivation are provided in accordance with the present invention by depositing a coating layer of silicate glass composition in a chemical vapor deposition process onto a spherical precursor substrate. (The term "silicate glass" as used herein refers to glass which includes oxides of silicon, either with or without other metallic oxides.) Density of the coated microcarrier product is closely controlled by appropriate selection of a substrate less than or equal to the desired product density and then controlling the thickness of the deposited glass coating (density $\simeq 2.3$ g/cc). The desired density of the microcarrier product will depend upon the density of the culture medium, the stir rate to be employed and the desired settling time. These factors, in turn, depend upon the type of cells being grown (e.g., tenacity of anchorage and ease of growth), the design of the processing vessel, and process requirements such as throughput. Most desirable shell density for a given process, as with other parameters, would typically be determined empirically. It is anticipated that the most desirable density range for microcarriers in accordance with the present invention will be equal to or greater than about 1.01 g/cc and less than or equal to about 1.2 g/cc.

In accordance with the method of the invention, the precursor substrate is selected to possess a density less than or equal to desired final density, preferably in the range of 1.01 to 1.2 g/cc, and for microcarrier applications has a diameter in the range of 50 to 500 $\mu$m. The preferred precursor substrates comprise hollow spherical shells of glass or ceramic composition, although solid beads of high-temperature plastic such as polyphenylene oxide (1.06 g/cc) are also contemplated. In the preferred method of the invention, a multiplicity of precursor substrates are placed as a fluidized bed within a reaction chamber. Gasses preheated to reaction temperature are separately fed into the reaction chamber and circulated through the bed so as to deposit on the individual precursor substrates a thin surface coating of silicate glass composition. The deposition process is continued for a time sufficient to bring the densities of the coated precursors to the desired final density within a range of 1.01 to 1.2 g/cc. A coating thickness of 11 to 16 $\mu$m is required for the ceramic and glass shells which are presently commercially available and inexpensive.

(For polyphenylene oxide, coatings of thickness about 1 μm are appropriate. Note that by modifying polyphenylene oxide by forming co-polymers, densities less than 1.06 g/cc are achievable.) The coated precursors are then removed from the reaction chamber. A modified implementation of the invention contemplates the use of plasma-, electron- or photo-assisted chemical vapor deposition techniques to obtain deposition at lower temperature. This modification permits the use of lower temperature plastics, and consequently a large range of precursor densities.

BRIEF DESCRIPTION OF THE DRAWING

The invention, together with additional objects, features and advantages thereof, will be best understood from the appended claims and from the following description read in conjunction with the accompanying drawing which is a schematic diagram of a presently preferred process for implementation of the invention.

DETAILED DESCRIPTION OF PREFERRED EMBODIMENTS

The method of the present invention contemplates, as a first step, selection of precursor substrates having a diameter in the range of 50 to 500 μm, and preferably in the range of 105 to 150 μm. The presently preferred implementation of the invention contemplates selection of commercially available hollow spherical shells of high-temperature glass or ceramic composition. For microcarrier applications, each batch of shells is culled and graded by diameter, preferably in the range of 105 to 150 μm, and by density, which should be less than or equal to desired final density. Any suitable classification and grading process may be employed. As an alternative, the shell precursors may be manufactured using any conventional technique, including the droplet generator or metal-organic-gel techniques disclosed, for example, in U.S. Pat. Nos. 4,017,290, 4,021,253, 4,133,854, 4,163,637, 4,257,798, 4,257,799, 4,336,338 and 4,340,407.

It is also contemplated and within the scope of the present invention in its broadest aspect to select as precursor substrates polymeric beads of so-called engineering high-temperature plastics composition, such as polyphenylene oxide, specifically poly(2.6-dimethylphenylene oxide). General Electric markets such as plastic composition under the trademark PPO, and also markets a polystyrene-plasticized modification under the trademark NORYL. Both of these products have a specific gravity of 1.06 g/cc.

Following such selection, the precursor substrates are surface-coated in a chemical vapor deposition process. For microcarrier applications, the precursor substrates are coated with a silicate glass for a time sufficient to raise the overall density thereof to the desired final density within the range of 1.01 to 1.2 g/cc. The drawing illustrates a system for performing such a deposition process. Referring to the drawing, a flow control system 10 of suitable valves and timers, etc. has inputs for receiving carbon dioxide and hydrogen from separate sources (not shown) at room temperature. Argon is input to system 10 for a preheat and purge operation to be described. (HCl may also be input to system 10 for calibration purposes.) Carbon dioxide and hydrogen are fed as selectable outputs of system 10 to a furnace 12. A bubbler 14 with a silicon tetrachloride supply is suspended in a water bath 16. A first conduit selectively supplies hydrogen as a transport gas to bubbler 14 through the three-way valves 15. A second conduit selectively supplies hydrogen to bypass bubbler 14. Both of such conduits, and the associated valves, etc. within system 10, are adapted to operate in the reverse direction so as to return argon to system 10 in the purge and preheat operation to be described.

A fluidized bed chemical vapor deposition coater 20 comprises a pipe 22 centrally bridged by a conical bed support 24 and thus essentially divided into an upper reaction chamber section 26 and a lower section 28. Lower section 28 is filled with a material such as quartz tubing and receives at its lowermost end the output or bypass from bubbler 14. An open hook-shaped capillary tube 30 extends into section 28 from the lower end of support 24. A center tube 32 extends downwardly through reaction chamber section 26 and terminates adjacent to bed support 24. The upper end of tube 32 receives the output of furnace 12. Reaction chamber 26 is vented to a dust collector 34, and thence through a filter 36 to a scrubber 38. The gaseous output of scrubber 38 is fed to a hood or vent, while the liquid phase output is fed to a beaker 40. Pipe 22 is enclosed within a furnace 42. A feed tube 44 is provided adjacent to the upper end of pipe 22 for introducing the precursor substrates.

In operation, furnace 12 is preheated to 1050° C. (less than the softening temperature of the precursors), and coater 20 is preheated by an argon purge from system 10 through furnace 12 and coater 20, and then back to system 10. When the target coating temperature is reached at coater 20, argon flow is terminated, a pre-weighed quantity of precursor shells is introduced through tube 44 to form a bed 46 surrounding the lower end of tube 32, and hydrogen flows are initiated at system 10. When temperatures have stabilized, carbon dioxide and silicon tetrachloride flows are initiated. Within furnace 12 the water-shift reaction occurs:

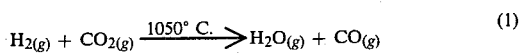

$$H_{2(g)} + CO_{2(g)} \xrightarrow{1050° C.} H_2O_{(g)} + CO_{(g)} \qquad (1)$$

The resulting mixture of steam and carbon monoxide is fed to coater input tube 32. In the meantime, silicon tetrachloride is transported by hydrogen to coater lower section 28 and preheated during passage through and around the material contained therein. The preheated mixture of hydrogen and silicon tetrachloride gas is fed by capillary 30 to bed 46. Thus, the reagant gases are preheated and fed separately to bed 46.

Within reaction chamber 26:

$$2H_2O_{(g)} + SiCl_{4(g)} \rightarrow SiO_{2(s)} + 4HCl_{(g)} \qquad (2)$$

The silicon dioxide is deposited as a surface layer on the shell substrates of bed 46, while the hydrogen chloride gas, together with hydrogen and carbon monoxide gasses, are vented to collector 34, filter 36 and scrubber 38. The hydrogen chloride is condensed, titrated and fed to beaker 40, which may thus be monitored to determine the amount of silicon dioxide produced within reactor chamber 26. When a predetermined quantity of hydrogen chloride ha been titrated, the carbon dioxide and silicon tetrachloride flows are terminated, the hydrogen flow is replaced by an argon purge, and bed 46 is allowed to cool and then removed.

The following Table summarizes the results of six "proof of principle" trial runs. (It should be noted that these trial runs were strictly for the purpose of demonstrating operability of the invention in production of satisfactory microcarriers, and that no effort was made to optimize any of the production variables.)

chamber, and makes possible the use of chemical vapor deposition processes with lower temperature plastic precursors.

TABLE 1

| Run | Shell Size, $\mu$m | Coating Time, min. | Target Coating Temperature, °C. | Reagent Concentration, m % | | | Total Flow, cc/min | Deposition Efficiency, % | Weight Percent of Coated Bed in Target Density Range, % |
| | | | | $CO_2$ | $SiCl_4$ | $H_2$ | | | |
| --- | --- | --- | --- | --- | --- | --- | --- | --- | --- |
| (1) | 105 to 149 | 150 | ~905 | 16.08 | 8.36 | 75.56 | 622 | 31.62 | 11.42 |
| (2) | 105 to 149 | 232 | ~950 | 18.30 | 8.49 | 73.21 | 683 | 46.51 | 4.30 |
| (3) | 125 to 149 | 203 | ~950 | 18.60 | 6.99 | 74.41 | 672 | 51.34 | 4.66 |
| (4) | 125 to 149 | 125 | ~950 | 18.17 | 9.16 | 72.67 | 688 | 41.56 | 6.73 |
| (5) | 125 to 149 | 65 | ~810 | 8.56 | 3.77 | 87.67 | 1460 | 9.01 | 9.19 |
| (6) | 125 to 149 | 125 | ~960 | 10.81 | 2.68 | 86.51 | 1156 | 69.81 | 5.17 |

Deposition efficiency (column nine) is the ratio of $SiO_2$ deposited on the microballoons to total $SiO_2$ generated, as indicated by titrated HCl. Target density (column ten) was 1.03 to 1.06 g/cc for runs (1) to (4) and 1.02 to 1.06 g/cc for runs (5) and (6).

In all runs, the hollow shell substrates were of silicate glass composition. In runs (5) and (6), the shells were pretreated in bed 46 in a CO—$SiCl_4$ atmosphere at 950° C. for fifteen minutes to make the precursors whiter. The resulting microcarriers were white in color, which is preferred by users.

Specifics of the vapor deposition process disclosed herein are exemplary. The following chemical vapor deposition reactions are also envisioned: (1) reaction of silane and oxygen at about 300° C.-500° C., (2) thermal decomposition of silane at about 600° C.-650° C., followed by oxidation of the outer surface, and (3) thermal decomposition of volatile metal-organic silicon compounds, such as tetraethyl ortho-silicate at about 350° C. Another important modification of the processes heretofore discussed contemplates so-called radiation assistance to the deposition processes. A source of plasma, electrons, photons or other suitable radiation, at the resonant frequency of one of the reaction gasses, is directed into the reaction chamber. Such radiation lowers the temperature required for reaction within the

I claim:

1. A microcarrier for anchorage-dependent cell cultivation in a culture medium comprising a hollow spherical shell of material selected from the group consisting of glasses and ceramics, and a discrete continuous non-porous surface layer of silicate glass composition entirely surrounding said shell, said microcarrier having a total composite density in the range of 1.01 to 1.2 g/cc.

2. The microcarrier set forth in claim 1 wherein said hollow spherical shell has a diameter in the range of 5 to 500 $\mu$m.

3. The microcarrier set forth in claim 2 wherein said hollow spherical shell has a diameter in the range of 105 to 150 $\mu$m, and wherein said surface layer has a thickness in the range of 11 to 16 $\mu$m.

4. A microcarrier for anchorage-dependent cell cultivation comprising a solid spherical bead of polyphenylene oxide having a diameter in the range of 50 to 500 $\mu$m, and a discrete continuous non-porous surface layer of silicate glass composition, the overall composite density of said microcarrier being in the range of 1.01 to 1.2 g/cc.

5. The microcarrier set forth in claim 4 wherein said bead is of poly(2.6-dimethylphenylene oxide) composition.

* * * * *